United States Patent [19]
Ranalletta et al.

[11] Patent Number: 5,368,496
[45] Date of Patent: Nov. 29, 1994

[54] CONNECTOR ASSEMBLY HAVING CONTROL LEVER ACTUATION

[75] Inventors: Joseph V. Ranalletta, Englewood, Colo.; Michael de Angeli, North Potomac, Md.

[73] Assignee: Tetrad Corporation, Englewood, Colo.

[21] Appl. No.: 164,578

[22] Filed: Dec. 10, 1993

[51] Int. Cl.⁵ .................................. H01R 13/15
[52] U.S. Cl. ................... 439/261; 439/372; 439/352
[58] Field of Search .............. 439/259, 261, 262, 310, 439/352, 362, 364, 372

[56] References Cited

U.S. PATENT DOCUMENTS

| | | | |
|---|---|---|---|
| 3,315,212 | 4/1967 | Peterson . | |
| 3,601,759 | 8/1971 | Barker | 439/262 |
| 4,061,408 | 12/1977 | Bast et al. | 439/263 |
| 4,630,874 | 12/1986 | Renn et al. | 439/263 |
| 4,768,969 | 9/1988 | Bauer et al. | 439/260 |
| 4,952,177 | 8/1990 | Drake et al. | 439/838 |
| 5,046,965 | 9/1991 | Neese et al. | 439/372 |
| 5,050,610 | 9/1991 | Oaks et al. | 128/660.01 |
| 5,069,215 | 12/1991 | Jadvar et al. | 128/642 |
| 5,105,818 | 4/1992 | Christian et al. | 128/662.06 |
| 5,109,851 | 5/1992 | Jadvar et al. | 128/642 |
| 5,123,855 | 6/1992 | Petersen | 439/263 |
| 5,147,213 | 9/1992 | Funk et al. | 439/266 |
| 5,217,383 | 6/1993 | Hildebrandt et al. | 439/259 |
| 5,310,352 | 5/1994 | Mroczkowski et al. | 439/372 X |

Primary Examiner—Khiem Nguyen
Attorney, Agent, or Firm—Michael M. de Angeli

[57] ABSTRACT

A connector mechanism for locking together first and second mating connector elements comprises a locking lever geared to rotate a locking rod returned by one of the connector elements. The tip of the locking rod extends into a mating recess in the other of the connector elements. When the rod is rotated, a helical member extending therearound slides along a cooperating arcuate member formed in the recess, locking the two elements together. The actuating rod is rotated by a control lever, enabling one-hand operation of the connector, and providing a readily ascertainable visual indication of the status of the connection. A locking member may be provided for preventing rotation of the lever except when the elements have been correctly assembled to one another.

27 Claims, 2 Drawing Sheets

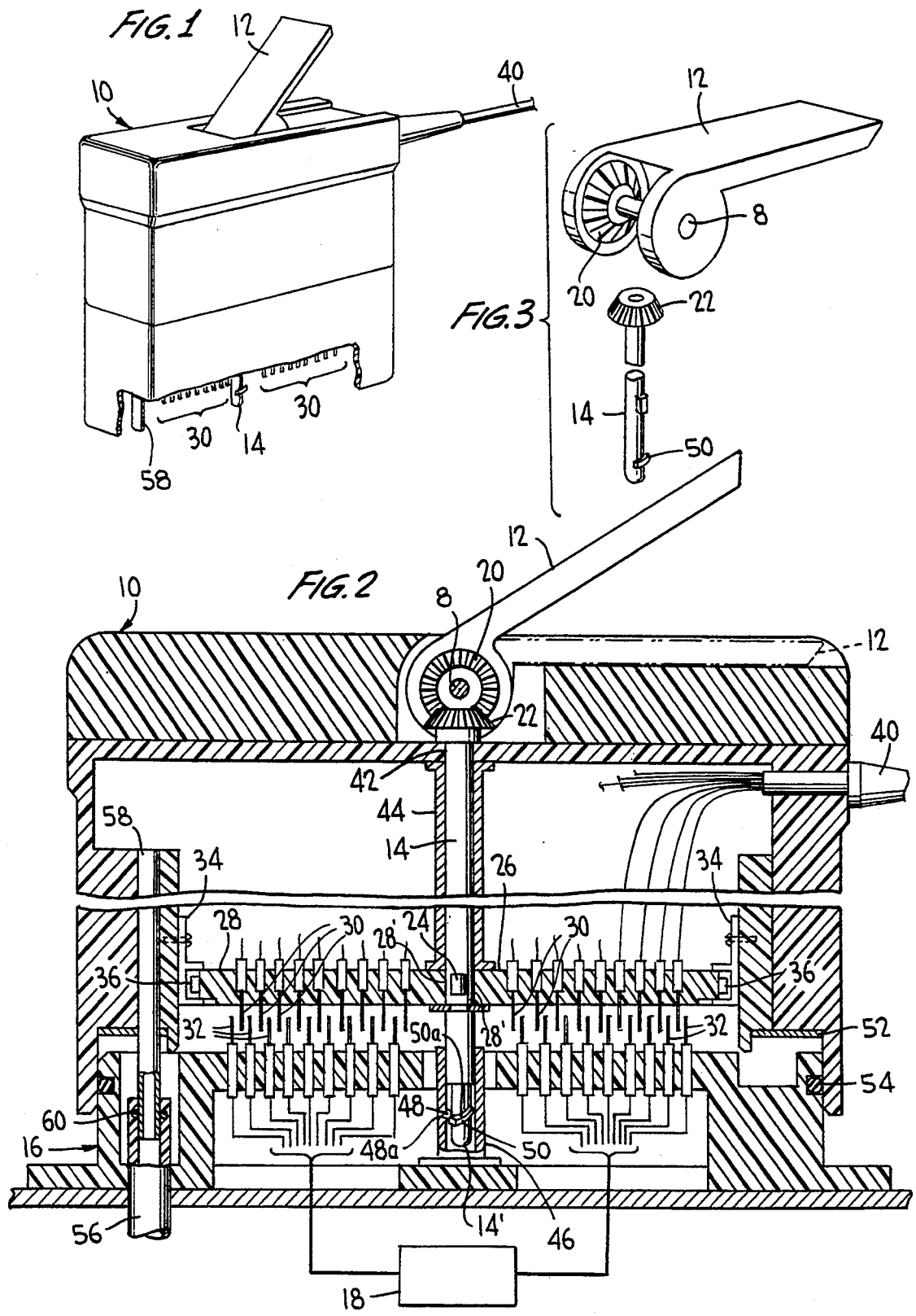

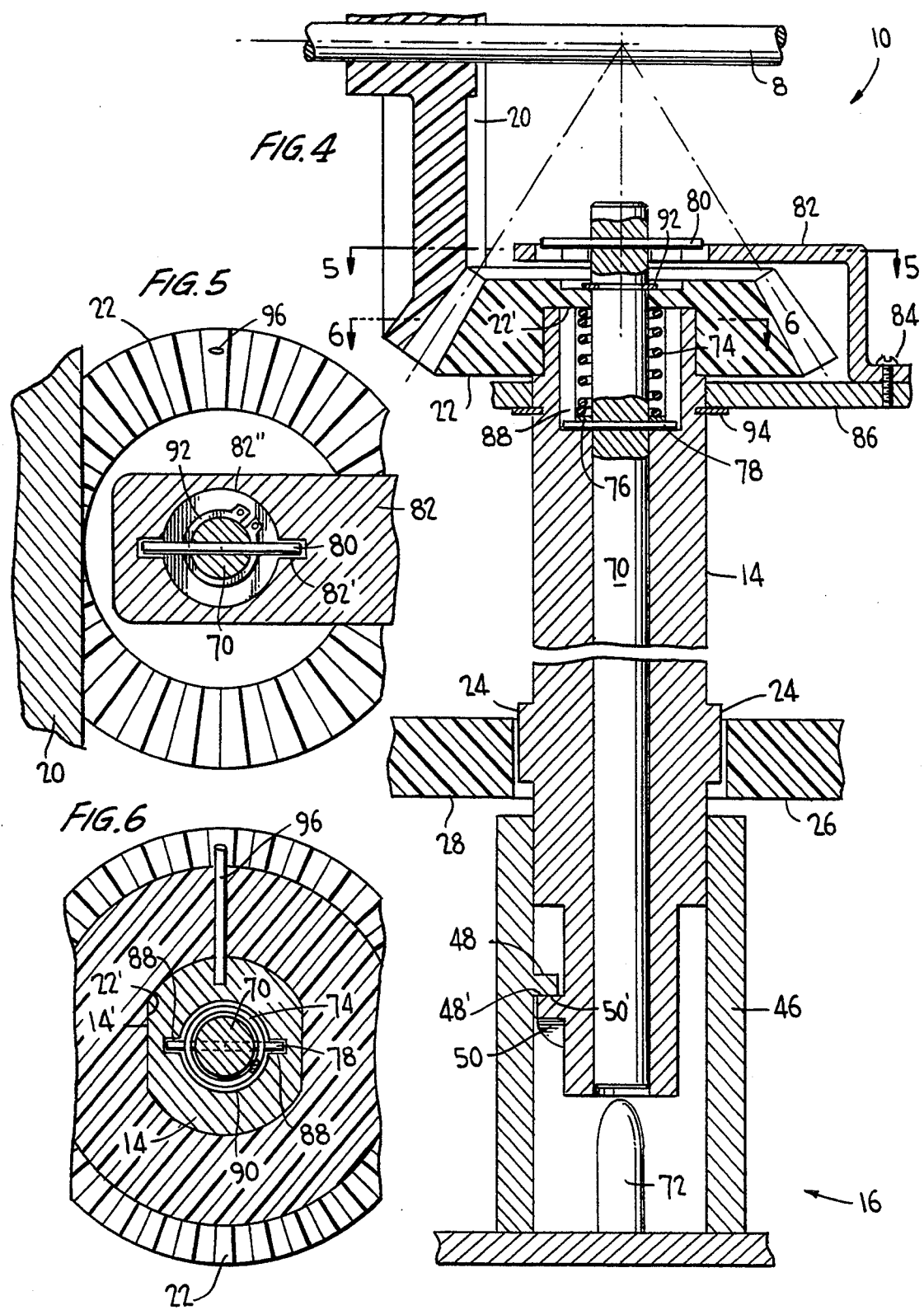

CONNECTOR ASSEMBLY HAVING CONTROL LEVER ACTUATION

FIELD OF THE INVENTION

This invention relates to an improved cable connector assembly. More particularly, this invention relates to a multi-pin connector structure having a locking lever for convenient actuation, and for providing a readily visible indication whether the connection has been effected.

BACKGROUND OF THE INVENTION

Multi-pin connectors are used throughout industry for connection of cables connecting electronic equipment. In many circumstances, such connectors are installed only once, that is, at the installation of a given piece of equipment, and thereafter need not be disturbed. However, other sorts of equipment require repetitive connection of cables, which may be required to be accomplished reliably under stressful conditions.

For example, many medical instruments now in use comprise probes connected by flexible cables to associated equipment, e.g., ultrasonic probes for endoscopic examination of patients. Such ultrasonic probes comprise a probe head including a transducer, and an elongated multiple-conductor cable. The cable connects the probe to associated equipment for providing ultrasonic drive signals to the transducer, such that the transducer transmits ultrasonic energy into a patient's body structure to be examined. The associated equipment also comprises signal processing circuitry for processing signals responsive to detected ultrasonic energy reflected from the patient's body structure and for providing a visible image responsive thereto. The probe cable is terminated by a multi-pin connector for connection to a mating connector on the associated equipment, or on an intermediate cable.

Frequently such surgical equipment is required to be connected for use under stressful conditions such in emergency care settings, battlefield situations, or the like. Any improvement simplifying use of this equipment or rendering it more reliable is of benefit; this is true in ordinary use, as well. The present invention is directed to improvements in the connectors used to connect such equipment.

More specifically, the multi-pin connectors used when repetitive disconnection and reconnection are not expected typically require "insertion force"—i.e., the contact elements of one element of the connector are biased so as to be moved upon insertion of the elements of the mating connector. The reliability of such connectors decreases as the number of disconnections and reconnections increases. Accordingly, where repetitive disconnections and reconnections are anticipated, as in connection of electrical equipment used for surgical purposes, so-called "zero insertion force"(ZIF) connectors are commonly used.

In ZIF connectors, the contacts of one of the mating elements of the connector pair, for example, the contact elements of a cable connector, are moved laterally responsive to operation of a control element, in order to engage stationary contacts of the other element of the connector pair. For example, when the cable connector is inserted into the mating connector, and the control element is operated, a control rod retained by the cable connector is rotated. A cam on the control rod moves one or more planar members carrying the contact elements of the cable connector laterally, so as to contact a number of mating contact elements comprised by the mating connector.

Many types of ZIF multi-pin connectors as now commonly used do not provide a simple visual indication whether the connection has been properly made, so that a glance is insufficient to determine whether the connection has been properly made. It is desired to improve available zero insertion force connectors to provide this capability.

At the same time, it is also desired to simplify the operation of such zero insertion force connectors, as commonly used for surgical probes and the like. Presently available zero insertion force connectors require two-hand operation, such that one hand is required to hold the cable connector into the mating connector, and a second hand is required to turn the control element. It would be desirable if ZIF connectors could be operated single-handedly.

It would also be desirable in some circumstances to provide a ZIF connector wherein the control element could not be operated unless the cable connector had been properly inserted into the mating connector, such that, if the control element had been operated, one could be certain that the connectors had been properly mated.

U.S. Pat. No. 5,050,610 to Oaks et al shows in FIG. 6 a conventional zero insertion force connector. A control element 54 is rotated through an angle to secure the cable connector 20 into the mating connector 52. Typically, the rotation of the control element rotates a control rod, such that a pin at the end of the rod is retained behind a keyhole-shaped opening in the mating connector 56. Two hands are required for this operation. Moreover, the position of control element 54 is ambiguous, i.e., it is difficult to determine by a glance at element 54 whether the control element is in the locked or released position.

Additional prior art generally relevant to the subject of connectors specifically addressing medical uses is provided by U.S. Pat. Nos. 5,046,965 to Neese, 5,069,215 and 5,109,851 to Jadvar, 4,952,177 to Drake et al, 4,061,408 to Bast et al, and 4,768,969 to Bauer. U.S. Pat. Nos. 5,123,855 to Petersen, 5,147,213 to Funk et al and 4,630,874 to Renn et al relate to zero insertion force connector assemblies. U.S. Pat. Nos. 3,315,212 to Peterson and 3,601,759 to Barker show multiple contact connector assemblies wherein cam locking mechanisms are provided.

None of the prior art just mentioned satisfies the needs of the art mentioned above.

OBJECTS OF THE INVENTION

Therefore, it is an object of the invention to provide an improved multi-pin connector particularly suitable for medical uses, wherein the position of a control lever actuated to lock the mating connector elements to one another provides a clear visual indication whether the connection has been properly effected.

A further object of the invention is to provide such a connector wherein the connection can be effected single-handedly.

Still a further object of the invention is to provide such a connector wherein the control element cannot be operated unless the cable connector has been properly inserted into the mating connector element.

A further object of the invention is to provide an improved cable connector satisfying the needs of the art mentioned above and further mating with pre-existing mating connectors, as conventionally provided on associated equipment or on intermediate connecting cables.

SUMMARY OF THE INVENTION

The present invention satisfies the needs of the art and objects of the invention mentioned above by its provision of an improved connector structure. The connector structure according to the invention comprises first and second mating elements meeting at a mating plane. The first of the elements defines a tubular recess for receiving the tip of a rotatable rod carried in the second element, and extending generally perpendicular to the mating plane. The distal tip of the rod is inserted into the recess as the elements meet. A downwardly-extending arcuate ridge is formed around the inner surface of the tubular recess providing a helical surface extending outwardly therefrom, while a member formed about the distal tip of the rod defines a cooperating helical surface, such that as the rod is inserted into the recess and rotated, the member on the rod slides along the arcuate ridge, pulling the mating connector elements together.

According to the invention, the rod is rotated by operation of a control lever pivoted to the cable connector about a pivot axis not coincident with the axis of rotation of the rod within the bore. The control lever and the rod comprise mating bevel gears such that pivoting of the control lever rotates the rod. The control lever is configured such that its position indicates whether the rod has been rotated within the recess, and thus whether the mating connector elements have been secured to one another, and such that the connection can be effected single-handedly.

In a further embodiment, the rod is precluded from rotation except when fully inserted into the tubular recess in the mating connector, such that if the control lever has been pivoted, the electrical contacts may be presumed to have been properly connected.

BRIEF DESCRIPTION OF THE DRAWINGS

The invention will be better understood if reference is made to the accompanying drawings, in which:

FIG. 1 shows a perspective view of a cable connector according to the invention;

FIG. 2 shows a cross section through the cable connector of the invention and through the mating connector, as disposed on associated equipment, or on an intermediate cable;

FIG. 3 shows an exploded perspective view of the control lever and actuating rod;

FIG. 4 shows a cross-section through the control rod in a second embodiment of the invention;

FIG. 5 is a cross-section taken along line 5—5 of FIG. 4; and

FIG. 6 is a cross-section taken along line 6—6 of FIG. 4.

DESCRIPTION OF THE PREFERRED EMBODIMENTS

As shown in FIG. 6 of U.S. Pat. No. 5,050,610 to Oaks et al, a zero insertion force cable connector as employed for connecting medical probes and the like to associated equipment typically comprises a control knob mounted on a proximal end of a rotatable actuating rod, the distal tip of which is received in a recess in a mating connector. The recess may have a keyhole-shaped opening, such that a transverse pin at the tip of the rod must be aligned in an entry position in order that the tip of the rod may enter the recess. When the control knob is thereafter rotated away from the entry position, the transverse pin is rotated to a position behind a portion of the structure surrounding the keyhole-shaped opening, confining the tip of the rod, and securing the mating elements to one another. As noted, it is difficult upon visual inspection to determine whether the control element has been thus rotated.

By comparison, as shown in FIG. 1, the improved connector of the invention 10 comprises a locking lever 12, pivoted from an upward or "open" position shown in FIGS. 1 and 2 to a downward or "closed" position shown in phantom in FIG. 2, in order to rotate a control rod 14 securing connector 10 to a mating connector 16. Thus, when the locking lever 12 is up, it can be determined at a glance that connector 10 is not securely connected to the mating connector 16; when the lever 12 is down, a glance is sufficient to determine that the rod 14 has been rotated to the locked position, such that if connector 10 has been correctly inserted into the mating connector 16, the connection has been properly effected.

Moreover, the control lever according to the invention as shown in FIG. 1 is much more convenient than that shown in the prior art as exemplified by FIG. 6 of the Oaks et al patent. In particular, as can be appreciated from review of FIG. 6 of the Oaks et al patent, inserting a conventional cable connector into a fixed connector and rotating the prior art control member is normally a two-handed operation; one hand is required to hold the cable connector into the fixed connector, and a second hand is required to rotate the control lever to lock the connectors together.

By comparison, the structure in FIG. 1 is readily operable by one hand; for example, while the fingers of one hand urge the connector 10 into the mating connector, the thumb or heel of that hand can readily push the lever 12 down, securing their connection.

As can be seen in FIG. 2, and with reference to FIG. 3, a first bevel gear 20 is formed on or fixed to control lever 12, which is pivoted about an axis defined by pivot pin 8, while a mating bevel gear 22 is similarly formed integrally with or fixed to control rod 14. These gears mesh as indicated in FIG. 2. Accordingly, when the control lever 12 is moved from its "up" or "unlocked" position shown in full in FIG. 2 to the "lower" or "locked" position shown in phantom in FIG. 2, rod 14 is rotated. When rod 14 is rotated, cam lobes 24 formed on the rod are urged against contact surfaces 26', 28' of members 26 and 28 which carry the electrical contacts 30 of the cable connector 10, moving members 26 and 28 laterally outwardly. Members 26 and 28 are supported at their edges for lateral movement, that is, toward and away from rod 14, by guides 34. Leaf springs 36 are disposed in guides 34, urging members 26 and 28 toward the cam lobes 24 formed on rod 14.

When planar members 26 and 28 are thus moved laterally outwardly upon rotation of rod 14, contacts 30 move laterally outwardly as well, in order to contact a second like plurality of electrical contacts 32 carried by the mating connector 16. The mating electrical contacts 32 are typically connected to associated equipment 18, e.g., for supplying control signals and the like to a probe connected to the distal end of cable 40 terminated by cable connector 10.

In one embodiment of the locking mechanism for securing the connector elements 10 and 16 to one another, rod 14 rotates within a bore 42 defined by the structure of the cable connector 10. The distal tip 14' of rod 14 fits within a tubular recess defined by a tubular member 46 mounted to a housing of connector element 16. An arcuate ridge 48 extends downwardly around the inner surface of tubular element 46, defining a helical surface 48' extending essentially transversely inwardly from the inner surface of tubular element 46. A corresponding arcuate member 50 is formed on the tip 14' of rod 14, defining a mating helical surface 50' extending essentially transversely outwardly from the distal tip 14' of the rod 14. Ridge 48 and arcuate member 50 thus cooperate to form a portion, typically between about 90° and about 180°, of a screw thread. Accordingly, if rod 14 is inserted into tubular recess 46, such that helical surface 50' contacts the cooperating helical surface 48', and rod 14 is inserted further while being rotated, member 50 slides along arcuate ridge 48, drawing the cable connector 10 into the mating connector 16.

Alternatively, the ridge 48 and mating arcuate member 50 may be supplanted by a pin extending transversely outwardly from the tip of pin 14, and received in an arcuate slot formed in tubular member 46. Other mechanisms for securing the cable connector 10 to the mating connector 16 upon pivoting of a control lever are within the invention. Specifically, the structure described above is considered equivalent to a comparable structure wherein a member extends transversely inwardly from the inner wall of recess 46 for cooperating with a helical surface formed on control rod 14.

It will be appreciated that the helical shapes of surfaces 48' and 50' cooperate such that the cable connector 10 is drawn into the mating connector 16 as rod 14 is rotated by operation of control lever 12. A resilient sealing member may be provided between confronting surfaces of the cable connector 10 and mating connector 16, e.g., at 52, so as to be compressed, forming a good seal therebetween upon operation of control lever 12. An additional seal 54 may also be provided if desired.

Other connections between the cable connector 10 and mating connector 16 can be made simultaneously. For example, the connector of the invention can be used to simultaneously connect a surgical probe comprising an internal lumen to a source of suction or aspiration. More particularly, suction or aspiration can be supplied to a conduit 56 provided as part of the fixed connector 16 and communicating with the lumen by way of tube 58, and sealed thereto by a further O-ring 60. This connection can be made at the same time electrical connection is made between the contact elements 30 and 32, respectively.

It will thus be appreciated that according to the invention, the awkward control element of the prior art, e.g., as shown in FIG. 6 of the Oakes et al patent, is replaced by a locking lever 12 according to the invention. Provision of the gearing elements comprised by bevel gears 20 and 22 allows motion of the locking lever through a small angle, e.g., approximately 30 degrees, to rotate the rod 14 through a larger angle, e.g., approximately 90 degrees, as needed to secure the connector element according to the invention to a mating connector.

In some circumstances of use, it may be desirable to preclude rotation of the control rod 14 unless the cable connector has been correctly inserted into the mating connector, such that the connection between the respective electrical contacts may be presumed to have been made if the control lever has been rotated. FIGS. 4–6 show a further embodiment of the invention providing this further capability. FIG. 4 is a view corresponding generally to FIG. 2, but taken through a plane at 90° to that of FIG. 2. Accordingly, FIG. 4 illustrates bevel gear 20 and pivot pin 8, as well as cams 24, in a view orthogonal to the view of FIG. 2.

In order to preclude control rod 14 from rotation until cable connector 10 has been fully inserted into mating connector 16, as provided in the embodiment of FIGS. 4–6, control rod 14 is bored longitudinally to receive an axially movable locking rod 70. A release pin 72 is mounted within tubular member 46, such that as cable connector 10 is seated fully within mating connector 16, release pin 72 urges locking rod 70 upwardly. When cable connector 10 is removed from mating connector 16, locking rod 70 is biased downwardly by a spring 74, confined between the undersurface 22' of bevel gear 22 and a washer 76 resting on a first transverse pin 78 fixed within a bore in locking pin 70. In this "locked" position, illustrated in FIG. 4, the ends of a second transverse pin 80 fixed within a second bore through locking pin 70 are confined within mating elongated portions 82' of an aperture 82" formed in a lock plate 82 fixed at 84 to the structure 86 of the cable connector 10. That is, while transverse pin 80 remains confined within the elongated portions 82' of aperture 82", locking rod 70 cannot be rotated with respect to structure 86 of cable connector 10. Gear 22 is retained on rod 70 by a spring clip 92 fitting into a groove on rod 70; the circular portion of the aperture 82" in plate 82 is provided in order that spring clip 92 can move upwardly with locking rod 70, as discussed below. The assembly of locking rod 70, gear 22, and control rod 14 is retained axially in position with respect to the structure 86 of cable connector 10 by being confined between a further spring clip 94 and the underside of plate 82.

As can be seen from examination of FIG. 6, the lateral tips of transverse pin 78 are received within axial recesses 88 extending laterally outwardly from a circular bore 90 in control rod 14 sized to receive washer 76; that is, the presence of the tips of transverse pin 78 within recesses 88 allows locking pin 70 to move axially within rod 14, but prevents their relative rotation. It will also be observed in FIG. 6 that gear 22 is precluded from rotation with respect to control rod 14 by the presence of cooperating flats formed thereon, at 22' and 14', respectively. A roll pin 96 may be inserted into aligned bores in gear 22 and rod 14, to secure their assembly. Accordingly, when locking rod 70 is prevented from rotation by the tips of transverse pin 80 fitting within elongated portions 82' of the aperture in plate 82, control rod 14 and gear 22 likewise cannot be rotated; accordingly, the control lever 12 cannot be operated while the cable connector 10 is withdrawn from the mating connector 16.

By comparison, when the cable connector 10 is fully inserted into the mating connector 16, release pin 72 forces locking rod 70 to slide axially upwardly within control rod 14. This lifts the transverse pin 80 out of the aperture 82' in plate 82, such that locking pin 70, control rod 14, and gear 22 can all be rotated by subsequent operation of control lever 12. At this point, surfaces 48' and 50' cooperate to pull cable connector 10 into mating connector 16, while cams 24 urge the contact-carrying members 26 and 28 laterally outwardly, both as described above. Thus, according to this aspect of the invention, if one is able to operate the control lever 12, one can conclude safely that the connectors are properly mated to one another, and that the electrical connections therebetween will be properly made.

It will be appreciated by those of skill in the art that cable connectors comprising locking rods operated by control levers according to the invention can be configured so as to be connected to mating connectors 16 generally conforming to the prior art, such that the improved cable connector 10 of the invention can be employed to make connections to pre-existing mating connectors 16 of various known types, although the invention is not so limited.

As noted above, the provision of a locking lever 12 according to the invention provides a visual indication of the locked or released status of the connection, and moreover enables simple one-hand operation of the connectors. To secure the cable connector 10 to a fixed mating connector 16, one can simply grip the cable connector 10 with one hand, urge the cable connector into the mating connector 16 and then close the locking lever 12 with the thumb, or possibly the heel, of one's hand. To release and remove the cable connector, one simply lifts the distal tip of the locking lever 12 with one's forefinger, thus releasing the cable connector 10 from the mating connector 16, and then pulls the cable connector 10 free of the mating connector 16.

It will further be appreciated that in the embodiment shown, the cable connector 10 and the mating connector 16 meet along a mating plane which generally includes the points at which the contacts 30 and 32 meet. Rod 14 extends perpendicular to this mating plane, while lever 12 is pivoted about a pivot pin 8 defining a pivot axis generally parallel to, but spaced from the mating plane. Further, it will be appreciated that the mating plane in this embodiment is generally rectangular, defining two shorter sides and two longer sides, and that the axis of the pivot pin 8 is generally transverse to the two longer sides. However, numerous modifications and improvements on the invention as thus described are within the scope of the invention. In particular, it would be possible to pivot the control lever about a pivot axis parallel to but spaced from the axis of rod 14, and gear the control lever to the rod 14 through spur gears.

Further modifications to the invention as disclosed specifically herein are similarly within its scope. Therefore, the present invention should not be measured by the above exemplary disclosure, but only by the appended claims.

What is claimed is:

1. In a mechanism for locking together first and second mating multi-pin connector elements, wherein a first of said elements comprises a member defining a generally tubular recess for receiving a distal tip of a control rod retained in a bore formed in the second of said elements and rotatable therein, and wherein said member and said rod cooperate such that said tip of said rod may be inserted into said recess and rotated through a predetermined angle in order to secure said tip of said rod within said recess, locking said first and second elements to one another, the improvement comprising:

a control lever mounted to said second element for pivoting about a pivot axis not coincident with the axis of rotation of said rod in said bore, and means operably connected to said control lever and said rod, such that upon pivoting of said lever said rod is rotated through a predetermined angle, whereby said rod may be secured within said recess, locking said first and second elements to one another.

2. The improvement of claim 1, wherein said mating elements meet along a generally planar mating plane, and said tip of said rod enters said recess along an axis substantially perpendicular to said mating plane.

3. The improvement of claim 1, wherein said control lever is pivoted about a pivot axis substantially perpendicular to said bore within which said rod is retained.

4. The improvement of claim 1, wherein said means operably connected to said control lever and said rod comprise intermeshing gearing elements including at least one gearing element fixed with respect to said lever, and a second gearing element fixed with respect to said rod.

5. The improvement of claim 4, wherein said control lever is pivoted about a pivot axis substantially perpendicular to said bore within which said rod is retained, and said gearing elements comprise meshing bevel gears, a first of said bevel gears being mounted on the pivot axis of said lever and fixed with respect to said lever, and a second of said bevel gears being fixed with respect to said rod.

6. The improvement of claim 1, wherein said first and second mating elements meet at a substantially rectangular mating plane having two longer sides and two shorter sides, and wherein said pivot axis about which said control lever pivots is parallel to said mating plane and transverse to the longer sides thereof.

7. The improvement of claim 1, wherein said tip of said rod comprises a member extending transversely with respect to the axis of rotation of said rod, and wherein a cooperating helical surface is defined within said recess, such that after said tip of said rod is inserted into said recess and rotated, said rod is drawn into said recess, locking said first and second elements to one another.

8. The improvement of claim 7, wherein said member extending transversely from said distal tip of said rod comprises means defining a helical surface extending generally transversely outwardly with respect to the axis of rotation of said rod.

9. The improvement of claim 1, further comprising means for preventing rotation of said control rod except after mating of said first and second elements to one another.

10. The improvement of claim 9, wherein said means for preventing rotation of said control rod except after mating of said first and second elements to one another comprises release means comprised by the first of said elements for releasing a locking means comprised by the second of said elements when the second of said elements is assembled to the first of said elements.

11. The improvement of claim 10, wherein said locking means comprised by the second of said elements comprises a locking member biased to prevent rotation of said control rod except when the second of said elements is assembled to the first of said elements.

12. A connector assembly for simultaneous connection of a plurality of electrical conductors, said assembly comprising first and second mating connector elements, said elements mating such that a plurality of first electrical contacts comprised by said first element meet a like plurality of second electrical contacts comprised by said second element substantially in a mating plane, and further comprising:

a recess defined by the first of said mating elements;

a bore formed in the second of said mating elements;

a rotatable control rod retained in said bore formed in the second of said mating elements;

mutually cooperating locking members comprised by said first of said mating elements and said rod, such that a distal end of said rod protruding from said second element may be inserted into said recess and rotated through a predetermined angle to lock said rod within said recess, and to secure said mating elements to one another;

a control lever mounted to the second of said elements by pivot means defining a pivot axis about which said control lever pivots, said pivot axis differing from the axis about which said rod rotates in said bore; and means operated by pivoting of said lever for rotating said rod, and thus controlling locking of said rod within said recess, and securing of said first and second elements to one another.

13. The connector assembly of claim 12, wherein said second element of said connector assembly comprises cam means operated upon rotation of said rod to move the second electrical contacts so as to engage the first electrical contacts upon rotation of said rod responsive to pivoting of said lever.

14. The connector assembly of claim 13, wherein said second electrical contacts move in said mating plane upon rotation of said rod responsive to pivoting of said lever.

15. The connector assembly of claim 12, wherein said tip of said rod enters said recess in a direction substantially perpendicular to said mating plane.

16. The connector assembly of claim 12, wherein said pivot axis about which said control lever is pivoted is substantially perpendicular to said axis about which said rod rotates in said bore.

17. The connector assembly of claim 12, wherein said means operably connected to said control lever and said rod comprises intermeshing gearing elements including at least one gearing element fixed with respect to said lever, and a second gearing element fixed with respect to said rod.

18. The connector assembly of claim 17, wherein said pivot axis about which said control lever is pivoted is substantially perpendicular to said axis about which said rod rotates in said bore, and said gearing elements comprise meshing bevel gears, a first of said bevel gears being mounted on the pivot axis of said lever and fixed with respect to said lever, and a second of said bevel gears being fixed with respect to said rod.

19. The connector assembly of claim 12, wherein said first and second mating elements meet at a substantially rectangular mating plane having two longer sides and two shorter sides, and wherein said pivot axis about which said control lever pivots is parallel to said mating plane and transverse to the longer sides thereof.

20. The connector assembly of claim 12, wherein said mutually cooperating locking members cooperating such that said tip of said rod may be inserted into said recess and rotated through a predetermined angle in order to secure said tip of said rod within said recess, locking said first and second elements to one another, comprise a member extending transversely from one of said distal tip of said rod and an inner confronting surface of said recess, and a cooperating helical surface formed on the other of said distal tip of said rod and said inner confronting surface of said recess, such that after said tip of said rod is inserted into said recess and rotated, said rod is drawn into said recess, locking said first and second elements to one another.

21. The improvement of claim 20, wherein said member extending transversely from one of said distal tip of said rod and an inner confronting surface of said recess comprises means for defining a helical surface extending generally transversely outwardly from said tip of said rod.

22. The improvement of claim 12, further comprising means for preventing rotation of said control rod except after mating of said first and second connector elements to one another.

23. The improvement of claim 22, wherein said means for preventing rotation of said control rod except after mating of said first and second elements to one another comprises release means comprised by the first of said elements for releasing a locking means comprised by the second of said elements when the second of said elements is assembled to the first of said elements.

24. In a mechanism for securing together first and second mating multi-pin connector elements, wherein a first of said elements comprises a member defining a generally tubular recess for receiving a distal tip of a control rod retained in a bore formed in the second of said elements and rotatable therein, and wherein said member and said rod cooperate such that said tip of said rod may be inserted into said recess and rotated through a predetermined angle in order to secure said tip of said rod within said recess, securing said first and second elements to one another, and further comprising a control lever mounted to said second element for pivoting about a pivot axis and operably connected to said rod, such that upon pivoting of said lever said rod is rotated through a predetermined angle, whereby said rod may be secured within said recess, locking said first and second elements to one another, the improvement comprising:

means for preventing rotation of said rod and pivoting of said control lever except when said tip of said rod has been inserted into said recess.

25. The improvement of claim 24, wherein said means for preventing rotation of said control rod except after mating of said first and second elements to one another comprises a release means comprised by the first of said elements for releasing a locking means comprised by the second of said elements when the second of said elements is assembled to the first of said elements.

26. The improvement of claim 25, wherein said locking means comprised by the second of said elements comprises a locking rod biased to prevent rotation of said control rod except when the second of said elements is assembled to the first of said elements.

27. The improvement of claim 25, wherein said locking rod is coaxial with and axially movable within said control rod, and wherein said release means comprises a pin disposed within said recess for urging said locking rod axially within said control rod against said bias when said tip of said control rod is inserted into said recess.

* * * * *